(12) United States Patent
Perreault et al.

(10) Patent No.: US 7,767,090 B2
(45) Date of Patent: Aug. 3, 2010

(54) SYSTEM FOR AUTOMATED COMPRESSION OF CHROMATOGRAPHY COLUMNS

(75) Inventors: Jeremy Perreault, Leominster, MA (US); Aaron Noyes, Cambridge, MA (US); Mark Carroll, Londonderry, NH (US)

(73) Assignee: Millipore Corporation, Billerica, MA (US)

(*) Notice: Subject to any disclaimer, the term of this patent is extended or adjusted under 35 U.S.C. 154(b) by 919 days.

(21) Appl. No.: 11/604,458

(22) Filed: Nov. 27, 2006

(65) Prior Publication Data

US 2007/0262021 A1 Nov. 15, 2007

Related U.S. Application Data

(62) Division of application No. 11/072,081, filed on Mar. 4, 2005, now Pat. No. 7,238,282.

(51) Int. Cl.
*B01D 15/08* (2006.01)
(52) U.S. Cl. .................... 210/656; 210/198.2
(58) Field of Classification Search ........... 210/635, 210/656, 659, 198.2; 95/82; 96/101; 422/70
See application file for complete search history.

(56) References Cited

U.S. PATENT DOCUMENTS

| | | | | |
|---|---|---|---|---|
| 3,410,135 A | | 11/1968 | Reynaud | 73/141 |
| 3,483,986 A | * | 12/1969 | Wright | 210/198.2 |
| 3,858,435 A | | 1/1975 | Stevens | 73/23.1 |
| 4,350,595 A | * | 9/1982 | Gunkel | 210/656 |
| 4,597,866 A | * | 7/1986 | Couillard | 210/198.2 |
| 5,158,676 A | * | 10/1992 | Kreher et al. | 210/198.2 |
| 5,462,659 A | * | 10/1995 | Saxena et al. | 210/198.2 |
| 5,951,873 A | | 9/1999 | Shalon et al. | 210/656 |
| 6,001,260 A | * | 12/1999 | Hatch et al. | 210/656 |
| 6,139,732 A | * | 10/2000 | Pelletier | 210/198.2 |

(Continued)

FOREIGN PATENT DOCUMENTS

BA 03/076923 9/2003

(Continued)

OTHER PUBLICATIONS

Japanese communication dated Feb. 10, 2009.

(Continued)

*Primary Examiner*—Ernest G Therkorn
(74) *Attorney, Agent, or Firm*—Nields, Lemack & Frame, LLC

(57) ABSTRACT

The present invention provides an automated system and method for maintaining compaction, and therefore increased efficiency, of a media bed within a chromatography column. In the preferred embodiment, an adjustment assembly is slidingly engaged inside one end of the column such that it can be moved along the column's major axis. When idle, the force exerted on this end is equal to the compression on the media. When the column is actively processing chromatographic fluid, this exerted force can be expressed as the sum of the compression on the media, and the force of the fluid being processed. This total force and the fluid pressure are monitored using a load cell and a pressure sensor respectively. The compression force operating on the media bed is then computed based on these measurements and compared to the optimal value. The position of the adjustment assembly within the column is then modified in response to changes in the measured compression force.

4 Claims, 4 Drawing Sheets

U.S. PATENT DOCUMENTS

| | | | |
|---|---|---|---|
| 6,843,918 B2 | 1/2005 | Hauck et al. | 210/656 |
| 7,132,053 B2 | 11/2006 | Hauck et al. | 210/656 |
| 2004/0099604 A1 | 5/2004 | Hauck et al. | 210/656 |
| 2004/0164012 A1* | 8/2004 | Dunkley et al. | 210/198.2 |

FOREIGN PATENT DOCUMENTS

| | | |
|---|---|---|
| JP | 63-62506 | 3/1988 |
| JP | 1-299460 | 12/1989 |
| WO | 97/32207 | 9/1997 |

OTHER PUBLICATIONS

The Indian communication dated Nov. 7, 2008.
The European communication dated Apr. 16, 2008.
Columns for Chromatography in Industrial Purification and Laboratory Use; Amicon a Grace company; Publication No. 531.
MicroPatent Search EP0008921; Column Chromatography and Like Processes and Apparatus for the Practice Thereof; Wright Scientific Limited.
Moduline Industrial Chromatography Column Operating Instructions; Publication No. I-287; Amicon a Grace Company.
The European Search Report dated Jul. 11, 2006.
Journal of Chromatography A, 741 (1996) 175-184; "Consolidation of the packing material in chromatographic columns under dynamic axial compression IV. Mechanical Properties of some packing materials" Brett J. Stanley et al.
Journal of Chromatography A., 989 (2003) 79-94; Martin Hofmann; "Use of ultrasound to monitor the packing of large-scale columns, the monitoring of media compression and the passage of molecules, such as monoclonal antibodies, through the column bed during chromatography".
The European Search Report dated Jul. 31, 2006.

* cited by examiner

SYSTEM FOR AUTOMATED COMPRESSION OF CHROMATOGRAPHY COLUMNS

This application is a divisional of U.S. patent application Ser. No. 11/072,081 filed Mar. 4, 2005 now U.S. Pat. No. 7,238,282, the disclosure of which is incorporated herein by reference.

BACKGROUND OF THE INVENTION

The present invention relates to chromatography columns and in particular to a chromatography column system and method of compressing and maintaining optimal or a consistent compression on a media bed within a chromatography column. Frequently it is desirable to separate out one or more useful components from a fluid mixture that contains other components that may not be useful or are less valuable. To accomplish this, it is often necessary or desirable to fractionate such a fluid mixture to separate out the useful or desired components. This can be carried out by using liquid chromatography systems. Liquid chromatography may be described as the fractionation of components of a mixture based on differences in the physical or chemical characteristics of the components. The various liquid chromatographic systems fractionate the components with a fractionation matrix. Some liquid chromatographic matrix systems fractionate the components of a mixture based upon such physical parameters as molecular weight. Still other liquid chromatographic systems will fractionate the components of a mixture based upon such chemical criteria as ionic charge, hydrophobicity, and the presence of certain chemical moieties such as antigenic determinants or lectin-binding sites on the components.

Chromatography systems of various sizes are used in both laboratory analysis operations and for industrial scale production operations in which separation steps such as separating out a fraction from human blood or separating out impurities from a pharmaceutical can be carried out on a large scale in a batch process.

Separations using chromatography columns filled with chromatographic media have been carried out for years. The chromatographic media typically comprises particles having a diameter between 5 and 100 μm. To maximize the effectiveness of the column, it is desirous to arrange the media as tightly and as uniformly as possible. This process, known as packing, eliminates voids and channels within the media. However, chromatography column packing, particularly where large columns are involved, is highly variable and can dramatically affect the efficiency of the separation. Many setup process parameters must be smoothly orchestrated in order to achieve a homogenous packed column. Depending on the size of the column, the packing process can take a significant amount of time, in the range of several hours. Yet despite the time invested in packing the column, often times less than 50% of these packed columns function in accordance with the specification.

During chromatography packing and operation, the compaction of the chromatographic media has a significant impact on the performance and repeatability of the column. In packing the column, typically the media is compressed through an alternating process of flowing liquid through the column to pack the media and then lowering the adjuster assembly in an effort to mechanically compress the media.

Once the column has been packed, the fluid to be fractionated is then passed through the column. During extended operation, packed media beds will experience a variety of issues with the media.

In some media, as it is wet with the packing and/or process fluid, it swells. This can cause an overcompression of the media potentially damaging the media or leading to a decrease in separation efficiency due to a reduction in the media pore sizes or availability of the media to the process stream.

Also a slight, but noticeable and cumulative bed compaction occurs. This is intrinsic to many packed bed columns. The sources of this further compaction are principally process-dependent and are generally due to the hydraulic drag of processing, flow perturbations during process cycles, mobile phase properties, such as flow rate, viscosity and density, support matrix swelling, and the intrinsic bead mobility in the packed bed superstructure. The magnitude of the compaction is also related to the size, shape and rigidity of the medium particles. For example, irregularly shaped particles such as PROSEP® matrix will be predisposed to de-bridging and the accompanying compaction.

The long-term result is that as a packed bed is repeatedly used, it incrementally compacts. This compaction leads to a continuous reduction in media bed density at the top of the bed, until a breach forms between the bed and the top bed support. The immediate performance implications are a decrease in separation efficiency, typically characterized by broader elution peaks with more tailing. Ultimately, this reduced bed density can lead to the formation of preferential flow channels through the bed, decreasing the effective life of the column, thereby necessitating more frequent repacking.

Therefore, there is a need for an improved method of maintaining proper compression within a packed chromatography column during operation, which will improve the performance of the column and extend its useful life.

SUMMARY OF THE INVENTION

The problems of the prior art have been overcome by the present invention, which provides an automated system and method for maintaining compaction, and therefore increased efficiency, of a media bed within a chromatography column. In the preferred embodiment, an adjustment assembly is slidingly engaged inside one end of the column such that it can be moved along the column's major axis. When idle, the force exerted on this end is equal to the compression of the media bed. When the column is actively processing, this exerted force can be expressed as the sum of the compression of the media, and the force of the fluid being processed. This total force and the fluid pressure are monitored using a load cell and a pressure sensor, respectively. The compression force operating on the media bed is then computed based on these measurements and compared to the desired or preferably optimal value. The position of the adjustment assembly within the column is then modified in response to changes in the measured compression force to maintain a consistent compression on the media bed.

DETAILED DESCRIPTION OF THE INVENTION

The repeated processing of a chromatography column generally will typically cause the further compaction of the previously packed media. This compaction can be significant. For example, in one trial, using media, repeated separation of a milieu of *E. Coli* proteins was performed. During the first separation process, the bed height was measured to be 56 cm. After the fortieth separation, the bed height had been compacted to a height of only 48 cm. This compaction led to a breach between the top surface of the media bed and the top bed support and decreased efficiency.

There is also a second issue associated with the bed height. The support matrices of the resins used in the media can change in volume. Each matrix possesses its own swelling behavior, with dextran-based and cellulosic resins being most susceptible to swelling when subjected to pH changes. Ionic strength also has a significant impact on the swelling of cellulosic, agarosic and dextran-based chromatography media such as ion exchangers. Generally, this swelling is most pronounced during the elution, regeneration, and most particularly the cleaning phases of a chromatographic separation cycle. Therefore, the column must be capable of adapting to swelling-induced changes in the media bed to prevent overpressurization of the column, or overstressing of the media.

Figure 3:
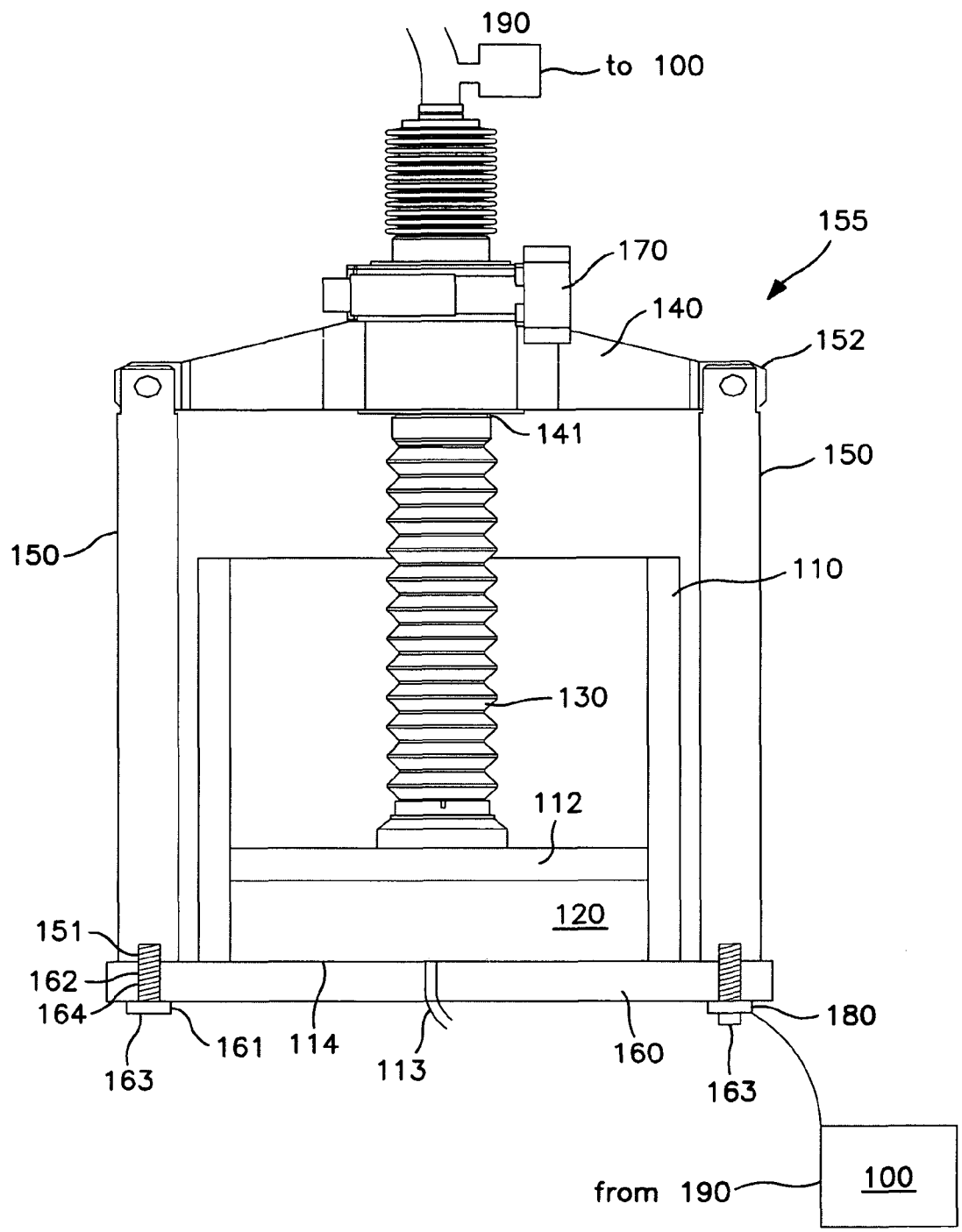
FIG. 3 is a cross sectional view of the preferred embodiment of the present invention.

FIG. 3 illustrates the preferred embodiment of the present invention. Before use, chromatography column 110 is filled with media slurry in a manner known to those skilled in the art. The adjustable bed support 112, which forms a tight seal along the walls of column 110, is then moved down inside the column tube 110. Typically, the adjustable bed support has a cross-sectional configuration that matches that of the column. Preferably, the bed support also has a gasket, or other sealing means along its perimeter to ensure the tightness of the seal. This allows the buffer within the column 110 to flow out the bottom flow port 113. Generally one bed support is fixed in place while the other is free to move. Alternatively, both supports can move if desired. In the embodiment as shown the bottom bed support 114 is fixed in place to the column. During this packing process, a media bed 120 forms and is contacted by the adjustable bed support as it continues to apply force to the bed 120. Thus, when the bed 120 is fully compacted, it exerts a force on adjustable bed support 112.

Adjustable bed support 112 is coupled to a shaft 130, which is preferably threaded. Shaft 130 passes through an opening 141 in yoke 140, which opening is also preferably threaded. Yoke 140 is held in position by stanchions 150, which are mounted to a base 160, on which the column 110 preferably rests. In the preferred embodiment, the stanchions 150 are held in contact with the base through the use of fasteners 161, such as bolts, which extend through openings 164 in the base and engage with the stanchion via slots 151 bored into the stanchion, which are also threaded. The fastener has a shaft 162, which is preferably threaded, of a given diameter, and a head 163 having a diameter larger than that of the shaft. The openings 164 in the base 160 are preferably larger than the diameter of the fastener's shaft 162, but smaller than the diameter of the fastener's head 163, to allow the fastener's shaft to move freely through the opening 164. The fastener 161 is inserted from the underside of the base 160, through the opening 164 such that the fastener's shaft 162 engages with the slot 151 in the stanchion 150.

Yoke 140 is affixed to a plurality of stanchions 150. Two stanchions typically provide the needed structural stability for smaller diameter columns, while additional stanchions may be used for large diameter columns. These stanchions 150 are preferably placed equidistant from one another around the circumference of a circle that is concentric to, but larger than column 110. The stanchions 150 have a height equal to, or preferably greater than, that of the column 110.

Figure 4:
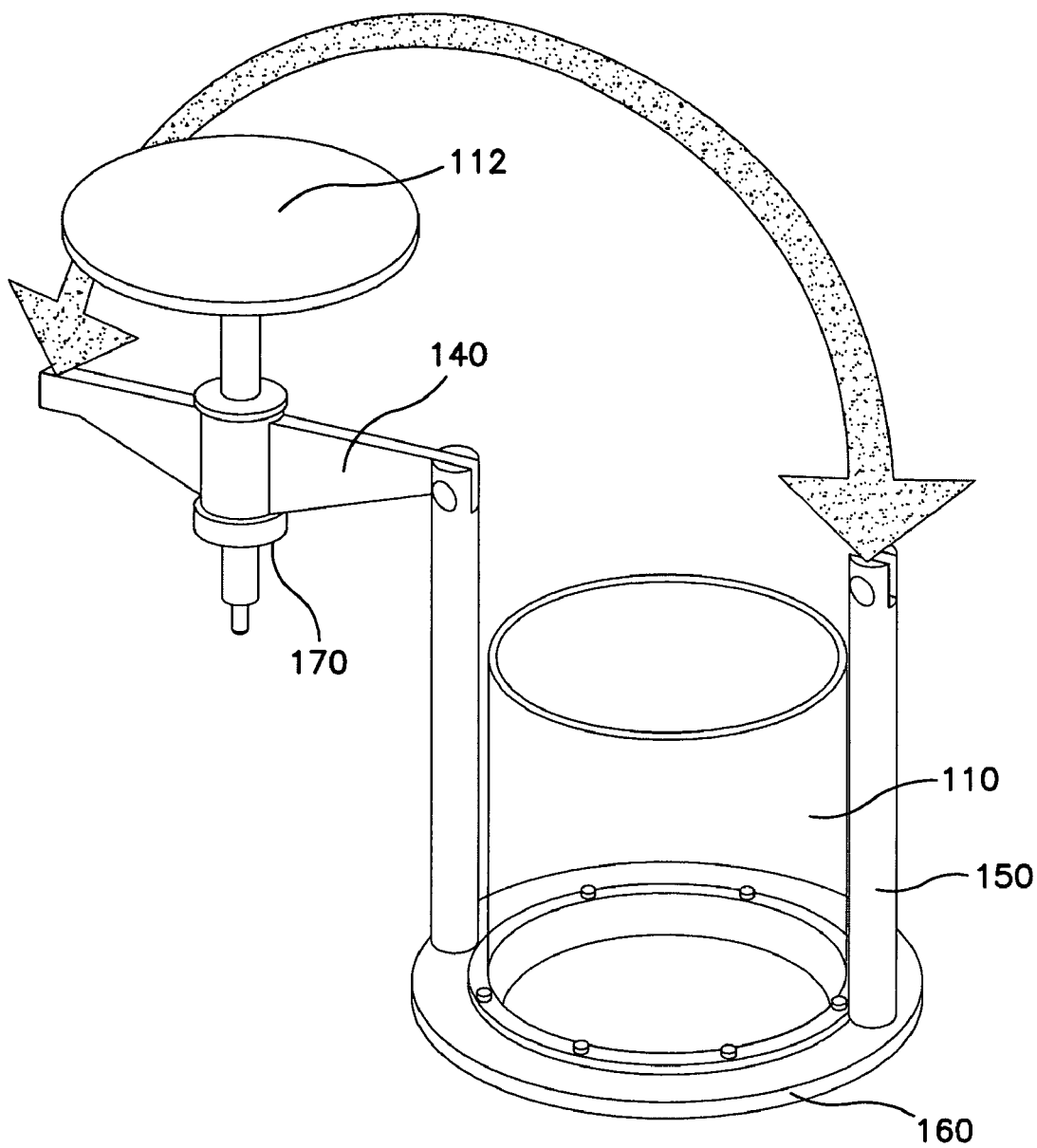
FIG. 4 shows the embodiment of FIG. 3 in the pivoted position.

In one embodiment, yoke 140 is connected to the two or more stanchions and it spans the width and centerline of the column 110. The yoke 140 is retained to the stanchions 150 by means such as slot 152, a ring or other device that can affirmatively hold the yoke 140 in place. The yoke 40 may be permanently attached to the stanchions 150 or more preferably, it may be removably connected to the stanchions 150 by bolts, clevis pins, cotter pins, clamps and the like. In one preferred embodiment, the yoke 40 is attached to one stanchion 50 by a bolt, and the other stanchion by a clevis pin so that when adjustable bed support 112 is withdrawn from the column, the yoke 140 can be pivoted vertically about stanchion 150 containing the bolt and moved up and out of the way of the column to allow easy access to the column interior. FIG. 4 shows that embodiment in the pivoted position.

In another embodiment, the yoke 140 can also rotate in a horizontal circular motion away from the mouth of the column 110.

Atop the yoke 140 is an actuator 170 adapted to move the shaft in the vertical direction, independent of the yoke 140. This actuator can be pneumatically, electrically or hydraulically controlled. In the preferred embodiment, a motor, preferably electrically powered, is equipped with a gear that contacts the threaded shaft 130. The movement of the motor causes the rotation of the gear, which in turn causes rotation of the threaded shaft 130. The resulting rotation of the threaded shaft 130, through the threaded opening 141 in yoke 140 causes the shaft 130 to move relative to the yoke 140 in the vertical direction.

The adjustable bed support 112, shaft 130, and actuator 170 comprise the adjuster assembly. These components operate in unison to adjust the position of the adjustable bed support 112 inside the column 110, thereby also controlling the pressure exerted on the media bed.

The yoke 140 and the stanchions 150 comprise a support structure 155. This structure is rigidly coupled and is affixed to the shaft 130 and the base 160, such that any force exerted on adjustable bed support 112 is transferred through shaft 130, through support structure 155, to the connection point between the support structure 155 and the base 160.

While this embodiment comprises a preferred embodiment in which a single shaft with 2 stanchions is used, the invention is not so limited. Those skilled in the art will appreciate that it is within the scope of the present invention to use multiple shafts and a greater number of stanchions. For example, a very large diameter column may require a greater number of shafts and stanchions in order to insure that the adjustable bed support descends uniformly and evenly onto the media bed.

Alternatively, other structures can be utilized. Chromatography columns are formed of three basic components; a column tube, a bottom fixed end and a top, movable end. See U.S. Pat. No. 4,350,595 and U.S. Pat. No. 6,139,732. The top end moves relative to the tube so as to be capable of removal for introduction and removal of chromatography media in the tube and to be capable of longitudinal travel into the tube to compress the media for use.

This top end however needs to be fixed at some point to the column in order to move relative to the column.

A first means for accomplishing this is to form a tube of high strength materials, including metals such as stainless steel or rigid structural plastics, such as acrylics or polymethylpentenes such as TPX® plastic available from Mitsui Petrochemical Industries Ltd Corporation of Japan. The tube has a flange at the upper end to which a top plate is attached to the column and a flange at the lower end to which a fixed bottom end is attached. The top, movable end is then attached to this top plate and travels relative to it in and out of the tube.

Figure 1:
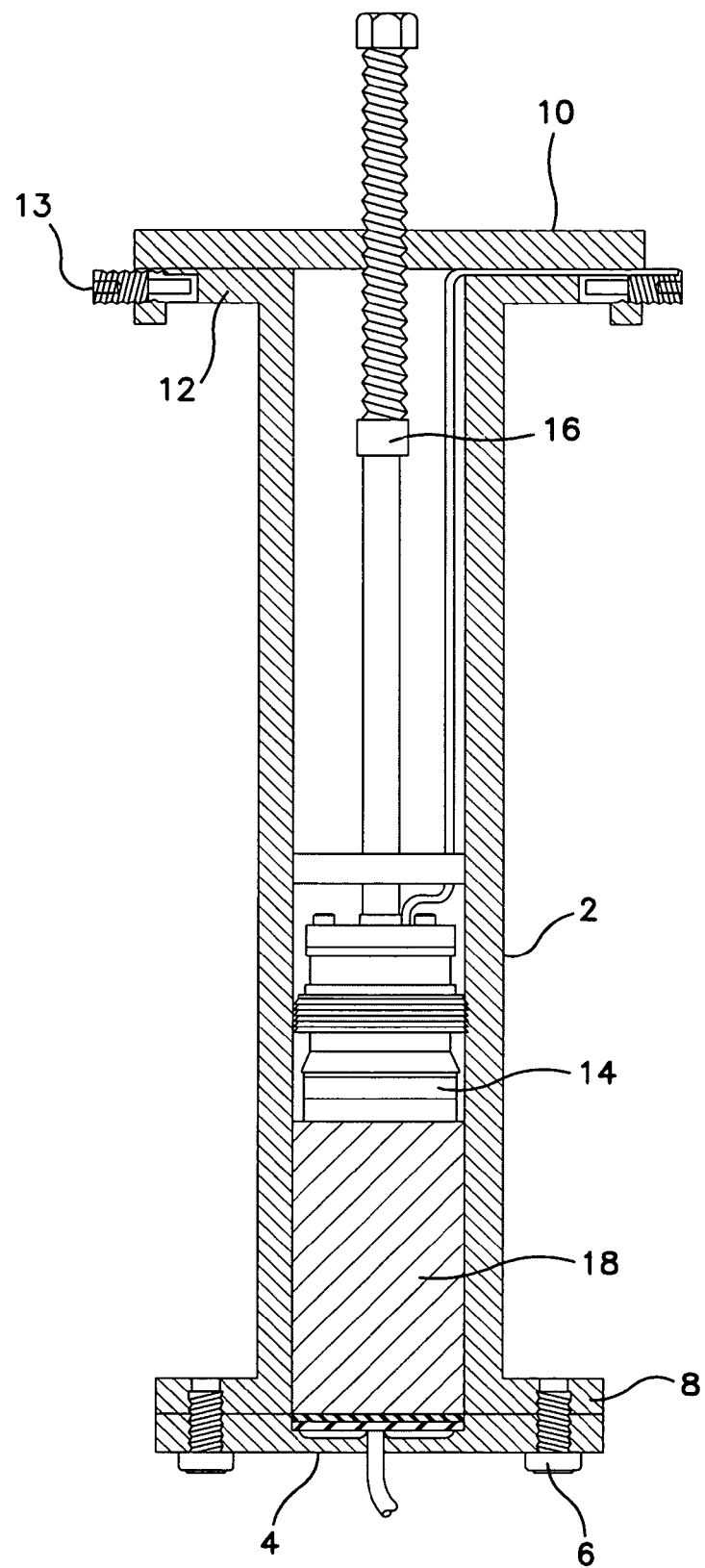
FIG. 1 is a cross sectional view of a first embodiment of the present invention.

In one embodiment, shown in FIG. 1, the tube 2 has a bottom plate 4 fixed in place by bolts 6 attached to a flange 8 of the tube 2. A top plate 10 is fixed to a top flange 12 of the tube 2 by setscrews 13. A movable end 14 is centrally located in the top plate 10 and is capable, by movement of rod 16, of moving into or out of the tube 2.

As the end 14 moves into the tube 2 to compress the media bed 18 for use, longitudinal forces are carried from the end 14 to the rod 16 to the top plate 10 and then to the tube 2 itself.

Figure 2:
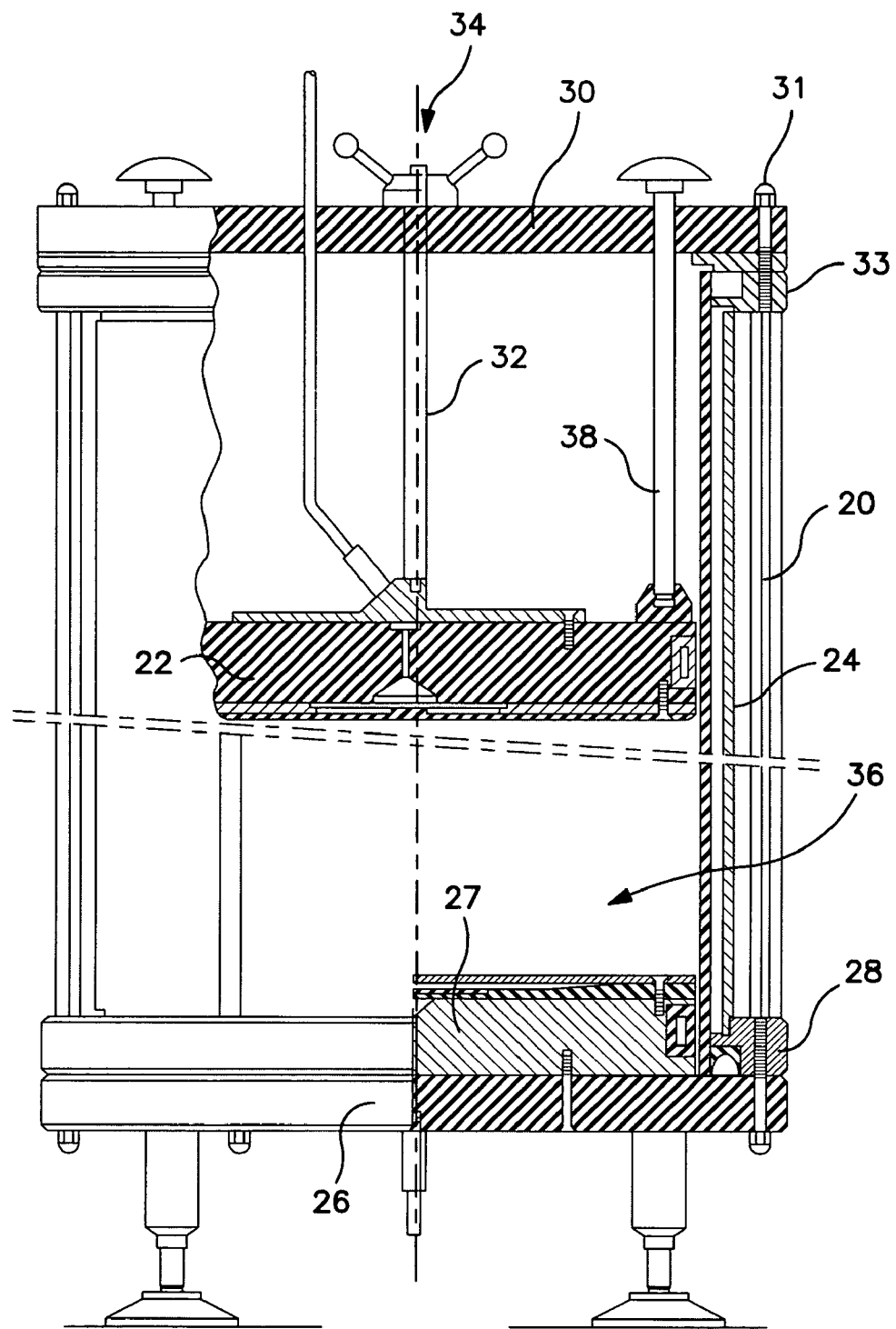
FIG. 2 is a cross sectional view of a second embodiment of the present invention.

Another alternative is shown in FIG. 2. It uses a series of rods 20 or screws closely aligned around the outside of the tube 24 to carry the longitudinal forces rather than the wall of the tube itself. This allows one to use less structurally rigid materials, such as glass or plastics, preferably acrylic or styrene, and to also use thinner walled tubes. All of this reduces the weight and cost of the device.

Most of the elements of that tube 24 of FIG. 2 are similar to those of FIG. 1. One has a movable top end plate 22, a bottom plate 26, attached to a fixed bottom end 27, flanges 28, either as part of the tube 24 or in this example as separate pieces to secure the fixed top plate 30 and bottom plate 26 to the tube 22. A rod 32 extends through the plate 30 and is connected to the movable end 22 by a handle 34. A bed of chromatography media 36 is compressed by the movement of the end 22. Also shown in FIG. 2 are a series of guide rods 38, which are used, in larger columns to keep the end 22 horizontal during movement. Plate 30 is normally affixed on flange 33 and attached by numerous mechanical fasteners 31.

In the preferred embodiment, a load cell 180 is located between the head 163 of the fastening device and the underside of base 160. However, the load cell 180 can be positioned in any location where it can measure the force exerted on the media bed. For example, the load cell can be positioned between bolt 6 and bottom plate 4 in FIG. 1. Similarly, the load cell can be located between mechanical fastener 31 and plate 30 or between mechanical fastener 31 and bottom plate 26 in FIG. 2. A load cell is a device that translates the load exerted on it into an analog electrical output, such as voltage or current. The relationship between the exerted load and the electrical output is well established and tightly controlled, such that the exact load experienced by the load cell can be determined by monitoring its electrical output. The term load cell is used herein to include any device that carries out this function.

Returning to FIG. 3, the load cell 180 is preferably circular, with a concentric opening in the middle, such that the diameter of the opening is large enough to allow shaft 162 to be slid through the opening. However, the diameter of the opening is preferably smaller than the diameter of the head 163 of the fastener, such that the head cannot pass through the opening, thereby causing the load cell to interconnect with the fastener in a similar manner as a traditional washer. Thus, the fastener is inserted through the concentric opening in the load cell 180, through the opening in the base 160, and into the slot of stanchion 150. Preferably, one load cell is used, regardless of the number of stanchions, however multiple load cells, or one load cell for each stanchion, are also envisioned as an embodiment of the present invention.

One skilled in the art will appreciate that although the preferred embodiment comprises an adjustable top bed support, and a fixed lower bed support, the invention is not so limited. The apparatus can also be constructed such that the top support is fixed, and the lower bed support is adjustable.

In the preferred embodiment, the fluid to be processed by the column 110 travels in a conduit through a hollow cavity within shaft 130 to adjustable bed support 112. Alternatively, the fluid may also travel in a conduit parallel to the shaft and then enter the adjustable bed support under a hollow arch formed at the base of the shaft. Adjustable bed support 112 also comprises a flow cell, which equally distributes the fluid such that it enters the media bed uniformly. The processed fluid then exits the column through bottom flow port 113. Those skilled in the art will appreciate that the direction of the fluid's travel is not limited to top to bottom; the fluid can also be forced into the bottom of the column and drawn out of the top surface. Similarly, it is not required that the fluid entry and the movable support be located in the same end of the column.

The pressure of the fluid entering the column is monitored. There are a number of methods known in the art for performing this monitoring. For example, a bubble trap can be inserted between the source of the fluid and the entrance to the shaft 130. A pressure sensor associated with the bubble trap can be used to supply the measured fluid pressure. In the preferred embodiment, a pressure sensor 190, preferably a transducer, is in communication with the fluid flow through the use of a T connection in close proximity to the shaft 130. A pressure transducer is used to convert a pressure measurement into either an analog or digital electrical signal, such as voltage or current. In this scenario, the transducer 190 measures the pressure of the fluid being forced through the conduit and into the column 110.

Having defined the components of the present invention, the operation now will be described. First, the media in the column is compressed to form a media bed. This process can be accomplished in a variety of ways well known to those skilled in the art, and the present invention is not limited to a specific packing methodology. Once the column has been packed, the adjustable bed support 112 will be in direct contact with the top of the bed 120, holding it under some amount of sufficient force to insure that it remains compacted. The media bed 120 exerts a counterforce onto the adjustable bed support 112. Since the adjustable bed support 112 is rigidly affixed to the shaft 130, which is rigidly affixed to the yoke 140, which is in turn rigidly affixed to the stanchions 150, this exerted force is transferred directly to the fastener 161 which is securing the stanchion 150 to the base 160. Thus, the force exerted by the media bed 120 is measurable by load cell 180, located between fastener 161 and the underside of the base 160. In the preferred embodiment, a single load cell is utilized, thus this load cell will experience only a fraction of the total force exerted by the media bed. That fraction is defined as 1/(# of stanchions). Thus, if two stanchions are utilized, the load cell will experience ½ of the total force exerted by the media bed 120. Alternatively, load cells can be placed in association with each stanchion. In this case, the total force would be defined as the sum of the forces experienced by each load cell. Similarly, if load cells are arranged on only a portion of the stanchions, the total load can be expressed as:

($\Sigma$ load cells)*(# of stanchions)/(# of load cells).

The outputs from the pressure sensor 190 and the load cell 180 are in communication with controller 100. Controller 100 also generates outputs to the actuator 170 directing it to alter the position of the adjustable bed support. By using the output from the load cell 180 in conjunction with controller 100, it is then possible to create a control system, whereby the load experienced by the load cell is used by the controller 100 to adjust the position of the shaft 130, using actuator 170. One skilled in the art will appreciate that the controller can be of various types, including, but not limited to proportional, proportional-derivative (PD), proportional integral (PI) or proportional-integral-derivative (PID), and that the invention is not limited by the choice of the controller. Similarly, the output from the controller 100 to the actuator 170 can be in various forms, including but not limited to analog voltage, current, digital signals, or pulses.

The optimal force to be applied to the media bed 120 can be determined using a number of different methods, such as but not limited to empirical measurements as the column is packed, or fixed values based on the amount and type of media being used. Once the optimal force required to create the proper compression on the media bed 120 is determined, the control system comprising the load cell 180, actuator 170 and controller 100 operate to maintain this force. The method of determining this optimal force is independent of the present invention, and therefore any method of determining this value is suitable.

Having established the proper compression for the media bed 120, the column is then ready to accept fluid. The fluid that enters the column will also be under pressure, and this pressure will also be exerted on the adjustable bed support. Therefore, the total force exerted on the adjustable bed support can be given by:

$$F_{Total} = F_{Fluid} + F_{Media\ Compression},$$

and $F_{Fluid}$ is given by:

$$F_{Fluid} = P_{Fluid} * Area_{Adjustable\ Bed\ Support}.$$

Combining these, the total force on the adjustable bed support is:

$$F_{Total} = P_{Fluid} * Area_{Adjustable\ Bed\ Support} + F_{Media\ Compression}.$$

Since the total force can be measured via the load cell, and the fluid pressure can be measured via the pressure sensor 190, it is possible to determine the amount of force being applied to the media bed.

$$F_{Media\ Compression} = F_{Total} - P_{Fluid} * Area_{Adjustable\ Bed\ Support}.$$

This computed $F_{Media\ Compression}$ is then compared to the optimal compression force. By adjusting the position of shaft 130 based on the measurement from the load cell 180 and the pressure sensor 170, it is possible to maintain a constant optimal pressure on the media bed 120. For example, as the media bed compresses, it will exert less force on the adjustable bed support 112. This reduction will be measured by the load cell as a decrease in total force (assuming a constant fluid pressure). The controller will detect this reduced force, and will determine that the force being exerted on the media bed has decreased. To compensate for this, the controller will actuate the actuator 170 to adjust the shaft 130 to further compress the column, until the media compression force returns to the optimal value. Conversely, if the media bed expands, the controller detects an increase in total force and will actuate the actuator 170 to retract the shaft 130 in a direction out of the column, until the media compression force returns to the optimal value.

The control system of the present invention can be utilized in a number of different ways. In a first embodiment, the control system is used only between separation cycles to correct for any changes in the height of the media bed 120 that occurred during the previous cycle. In this embodiment, the position of the adjustable bed support within the cylinder is held constant throughout the separation cycle, and then its height is adjusted after the completion of the cycle.

In a second embodiment, the control system is continuously operational, thereby constantly adjusting the pressure exerted on the media bed by changing the position of the adjustable bed support within the cylinder. Due to the precision required, this embodiment preferably utilizes a PID controller. One skilled in the art will recognize that a continuous control system can be approximated through the use of a sampled system, whereby the load cell and pressure transducers are sampled at periodic intervals and adjustments to the vertical position of the adjustable bed support are made in response to these sampled measurements.

What is claimed is:

1. The process of maintaining compression on a media bed in a chromatography system, said system comprising a column having an inlet and containing a media bed through which a fluid is adapted to flow; an adjustable bed support movable in said column and adapted to exert a force on said media bed; a sensor for determining the pressure of said fluid entering said column; a load cell for measuring the force exerted on said adjustable bed support; and an actuator for moving said adjustable bed support in response to the force measured by said load cell, said process comprising the steps of:

using said load cell to measure said force exerted on said adjustable bed support;
using said sensor to measure the pressure of said fluid;
calculating compression force on said media bed, based on measurements from said load cell and said sensor;
comparing said calculated compression force to an optimal compression force; and
using said actuator to move said adjustable bed support based on said comparison.

2. The process of claim 1, wherein said steps are performed between each separation cycle.

3. The process of claim 1, wherein said steps are performed continuously.

4. The process of claim 1, wherein said steps are performed at regular time intervals.

* * * * *